United States Patent [19]

Nagarajan et al.

[11] Patent Number: 4,643,987

[45] Date of Patent: Feb. 17, 1987

[54] MODIFIED GLYCOPEPTIDES

[75] Inventors: Ramakrishnan Nagarajan; Amelia A. Schabel, both of Indianapolis, Ind.

[73] Assignee: Eli Lilly and Company, Indianapolis, Ind.

[21] Appl. No.: 765,422

[22] Filed: Aug. 14, 1985

[51] Int. Cl.$^4$ .................. A61K 37/00; C07K 9/00
[52] U.S. Cl. ........................... 514/8; 530/322
[58] Field of Search ................ 514/8; 530/322

[56] References Cited

U.S. PATENT DOCUMENTS

| | | | |
|---|---|---|---|
| 3,067,099 | 12/1962 | McCormick et al. | 167/65 |
| 4,495,179 | 1/1985 | Hoehn et al. | 514/9 |
| 4,497,802 | 2/1985 | Debono | 514/8 |
| 4,547,488 | 10/1985 | Merkel | 514/10 |
| 4,548,925 | 10/1985 | Higgins, Jr. et al. | 514/10 |

OTHER PUBLICATIONS

Harris et al., "Structure of the Glycopeptide Antibiotic Vancomycin. Evidence for an Asparagine Residue in the Peptide," *J. Am. Chem. Soc.* 104, 4293–4295 (1982).
Pfeiffer, "Structural Features of Vancomycin," Reviews of Infectious Diseases, vol. 3, Suppl., S205–S209 (Nov.–Dec. 1981).
Perkins, "Specificity of Combination Between Mucopeptide Precursors and Vancomycin or Ristocetin," *Biochem. J.* 111, 195–205 (1969).
Derwent Abstract No. 84-160164/26 (Eli Lilly and Company) of European Pat. No. 112-184-A (Jun. 27, 1984).

*Primary Examiner*—Delbert R. Phillips
*Attorney, Agent, or Firm*—Nancy J. Harrison

[57] ABSTRACT

Novel aracyl glycopeptide derivatives of formula 1 and methods for their preparation from the glycopeptide antibiotics vancomycin, A51568A, A51568B, M43A and M43D, are provided. The new glycopeptide derivatives are useful antibacterial agents.

24 Claims, No Drawings

MODIFIED GLYCOPEPTIDES

SUMMARY OF THE INVENTION

This invention relates to new glycopeptide derivatives of formula 1:

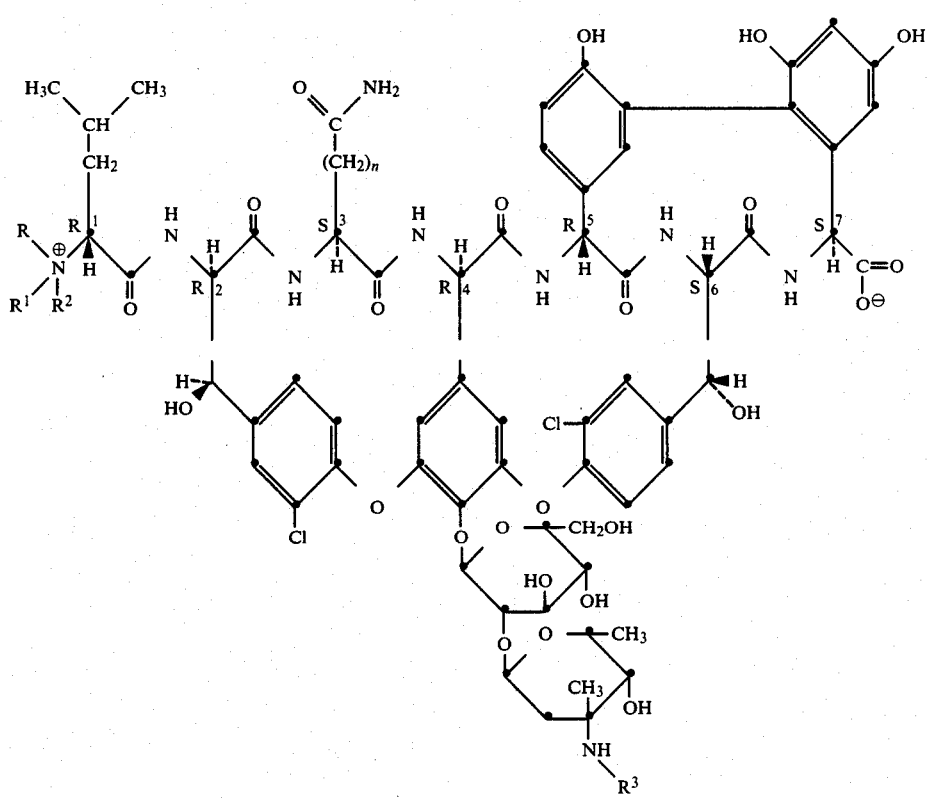

wherein
R and $R^1$ are hydrogen or methyl;
$R^2$ is methyl or $R^3$;
$R^3$ is hydrogen or an acyl group of the formula $$-\overset{O}{\underset{\|}{C}}-(W)_m-(A^1)_p-\underset{\underset{X}{|}}{Ar}-(A)_qR^4$$

wherein
Ar is a group selected from phenyl, cyclohexadienyl, cyclohexenyl, naphthyl, thienyl, furyl, thiazolyl or pyridinyl;
A is divalent oxygen, sulfur, sulfinyl, or sulfonyl;
$A^1$ is A or —NH—;
X is hydrogen, halo, nitro, $C_1$-$C_3$-alkyl, hydroxy, $C_1$-$C_3$-alkoxy, mercapto, $C_1$-$C_3$-alkylthio, carbamoyl, $C_1$-$C_3$-alkylcarbamoyl, $C_1$-$C_4$-alkoxycarbonyl, $C_1$-$C_4$-alkanoyl, carboxy, or $R_5R_6N$—;
$R^4$ is hydrogen, $C_1$-$C_{18}$-alkyl or $C_2$-$C_{18}$-alkenyl;
$R^5$ and $R^6$ independently are hydrogen or $C_1$-$C_4$-alkyl, or
$R^5$ is hydrogen and $R^6$ is an amino-protecting group;
W is $C_1$-$C_{10}$-alkylene or $C_2$-$C_{10}$-alkenylene;
n is 1 or 2; and
m, p and q are 0 or 1,
provided that: (1) the sum of the carbon atoms in the $R^4$ and W groups cannot exceed 21; (2) when X is mercapto, A and $A^1$ cannot be sulfinyl or sulfonyl; (3) when A and $A^1$ are sulfinyl or sulfonyl, they must be in equal oxidation states; (4) at least one of $R^2$ and $R^3$ must be other than hydrogen; (5) if m=0, p must=0; and (6) when n is 2, R and $R^1$ must be hydrogen; and to the salts of these compounds.

The formula 1 compounds have excellent antibacterial activity, especially against Gram-positive microorganisms. Thus, useful compositions containing the formula 1 compounds and methods of treating infections using the formula 1 compounds are also aspects of this invention.

DETAILED DESCRIPTION

This invention relates to new N-acyl glycopeptide derivatives having formula 1 and to methods for preparing these derivatives. The formula 1 compounds have useful antibacterial activity.

New, improved antibiotics are continually in demand, particularly for the treatment of human diseases. Increased potency, expanded spectrum of bacterial inhibition, increased in vivo efficacy, and improved pharmaceutical properties (such as greater oral absorption, higher blood or tissue concentrations, longer in vivo half life, and more advantageous rate or route of excretion and rate or pattern of metabolism) are some of the goals for improved antibiotics.

In the search for new antibiotics, structural modification of known antibiotics is attempted whenever possible. Many antibiotics, including the glycopeptides, however, have such complex structures that even small changes are difficult to make. Furthermore, it is difficult to predict the effect these changes will make in the activity. Processes for modifying known antibiotics and the new active derivatives made by such processes, therefore, continue to be of great importance.

The formula 1 compounds are new members of the glycopeptide group of antibiotics. The compounds are prepared from the known glycopeptides vancomycin (see, for example, U.S. Pat. No. 3,067,099), antibiotic A51568 factor A (see U.S. Pat. No. 4,495,179) and A51568 factor B (see the copending application of L. D. Boeck, M. M. Hoehn and G. G. Marconi, Ser. No. 561,008, filed Dec. 13, 1983); antibiotic M43A (see the copending application of Harvey M. Higgins, Mack H. McCormick and Kurt E. Merkel, Ser. No. 600,729, filed Apr. 16, 1984), and antibiotic M43D (see the copending application of Kurt E. Merkel, Ser. No. 600,725, filed Apr. 16, 1984). The structural formulas of these glycopeptide antibiotics are shown in formulas 2–6 which follow:

amino group during an acylation reaction. Such groups are well recognized so that selecting a suitable group for this purpose will be readily apparent. (See, for example, "Protective Groups in Organic Chemistry," M. McOmie, Ed, Plenum Press, New York, 1973). The tert-butoxycarbonyl (tBOC) and carbobenzyloxy (Cbz) groups are examples of suitable amino-protecting groups.

The formula 1 compounds are shown as zwitterions. Those in the art will recognize, however, that each has groups which can react to form various salts. All such forms of the formula 1 compounds are part of this invention. The salts are useful, for example, for separating and purifying the antibiotics. In addition, the salts have an improved solubility in water.

The formula 1 salts are prepared using standard procedures for salt preparation. For example, the zwitter-

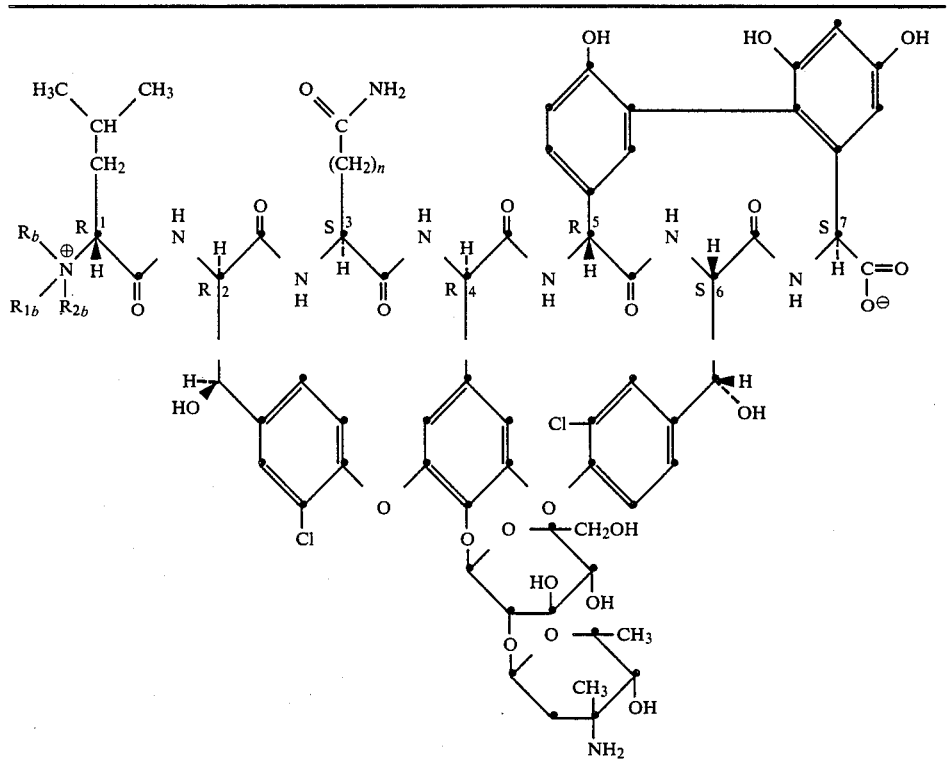

| Compound No. | Compound | $R_b$ | $R_{1b}$ | $R_{2b}$ | n |
|---|---|---|---|---|---|
| 2 | Vancomycin | $CH_3$ | H | H | 1 |
| 3 | M43A | $CH_3$ | $CH_3$ | $CH_3$ | 1 |
| 4 | M43D | $CH_3$ | $CH_3$ | H | 1 |
| 5 | A51568A | H | H | H | 1 |
| 6 | A51568B | H | H | H | 2 |

It will be appreciated that the sugar groups in formulas 1 and 3–6 have the same configuration as do those in vancomycin, i.e., α-O-vancosaminyl-β-O-glucosyl.

As used herein, the terms "alkyl", "alkenyl", "alkoxy", "alkylthio" and "alkanoyl" refer to both straight, branched or cyclic hydrocarbon chains.

The term "alkenyl" refers to an unsaturated group containing not more than three double bonds. The double bonds of the alkenyl group may be in either the cis or trans configuration.

The term "halo" refers to chloro, bromo or iodo.

The term "amino-protecting group" refers to those groups known in the art to be suitable for protecting an ion can be neutralized with an appropriate acid to form an acid addition salt.

The formula 1 acid addition salts are particularly useful. Representative suitable salts include those salts formed by standard reactions with both organic and inorganic acids such as, for example, sulfuric, hydrochloric, phosphoric, acetic, succinic, citric, lactic, maleic, fumaric, cholic, pamoic, mucic, D-glutamic, d-camphoric, glutaric, glycolic, phthalic, tartaric, formic, lauric, stearic, salicylic, methanesulfonic, benzenesulfonic, sorbic, picric, benzoic, cinnamic and like acids.

Pharmaceutically acceptable acid addition salts of the formula 1 compounds are an especially preferred group of salts of this invention.

The formula 1 compounds are prepared from the glycopeptide antibiotics vancomycin, A51568A, A51568B, M43A and M43D by reacting the antibiotic (a) at the amino group of the sugar vancosamine; (b) at the amino group of the leucine moiety; or at both (a) and (b) with the appropriate

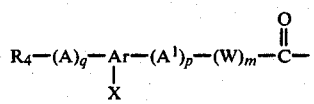

group, using methods conventional in the art of forming an amide bond. The acylation is accomplished, in general, by reacting the antibiotic with an activated derivative of formula 7:

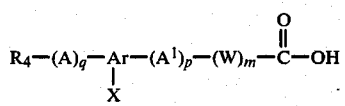

corresponding to the desired acyl side chain group.

The term "activated derivative" means a derivative which renders the carboxyl function of the acylating agent reactive to coupling with the amino group to form the amide bond. Those in the art will recognize suitable activated derivatives, methods for preparing them and methods for using them as acylating agents. Preferred activated derivatives are: (a) an acid halide (e.g., acid chloride), (b) an acid anhydride (e.g., an alkoxyformic acid anhydride) or (c) an activated ester (e.g., a 2,4,5-trichlorophenyl ester). Other methods for activating the carboxyl function include reaction of the carboxylic acid with a carbonyldiimide (e.g., 1,3-dicyclohexylcarbodiimide or 1,3-diisopropylcarbodiimide) to give a reactive intermediate which, because of instability, is not isolated, the reaction with the amine being carried out in situ.

A preferred method for preparing the compounds of formula 1 is by the active ester method. The use of a trichlorophenyl ester of the desired acid as the acylating agent is most preferred. In this method, an excess amount of the active ester is reacted with the parent antibiotic at room temperature in a non-reactive organic solvent such as N,N-dimethylformamide (DMF). The reaction time is not critical, although a time of about 6 to about 20 hours is preferred. At the conclusion of the reaction, the solvent is removed. The residue is purified, for example, by reversed phase HPLC using LP-1/C18 as the stationary/phase and a mixture of $H_2O/CH_3CN$ as the solvent system.

The formula 7 acids used as starting materials for the acylation reaction, and their activated derivatives (in particular, the acid chlorides and the trichlorophenyl esters), either are known compounds or can be prepared from known compounds by known methods. The trichlorophenyl esters are conveniently made by treating the acid chloride of the formula 7 acid with a trichlorophenol in the presence of pyridine or by treating the free acid with a trichlorophenol in the presence of 1,3-dicyclohexylcarbodiimide used as a coupling agent. The trichlorophenyl ester derivatives can be purified, for example, by column chromatography over silica gel in toluene.

In subgeneric aspects, the following formula 1 compounds are preferred embodiments of this invention:

1a: Compounds wherein $R^2$ is hydrogen and $R^3$ is an acyl group.

1b: Compounds wherein $R^3$ is hydrogen and $R^2$ is an acyl group.

In addition, of special interest are those 1a and 1b compounds wherein:
(1) R=methyl; $R^1$ and $R^2$=hydrogen;
(2) R, $R^1$ and $R^2$=methyl; and
(3) R, $R^1$ and $R^2$=hydrogen.

Especially preferred are 1a compounds wherein:
(1) m and p=0
(2) m, p and q=0
(3) m and p=0 and q=1
(4) m and p=0; q=1; and A=oxygen
(5) Ar=phenyl.

Illustrative compounds of this invention are listed in Table I.

TABLE I

Illustrative Formula 1 Compounds[a]

| Compound No. | R | $R^1$ | $R^2$ | $R^3$ |
|---|---|---|---|---|
| 1 | Me | H | H | 4-(n-octyloxy)benzoyl |
| 2 | Me | H | H | 4-(n-octyl)benzoyl |
| 3 | Me | H | 4-(n-octyl)benzoyl | H |
| 4 | Me | H | H | 4-methoxybenzoyl |
| 5 | Me | H | 4-methoxybenzoyl | H |
| 6 | Me | H | H | 1-oxo-4-phenoxy-n-butyl |
| 7 | Me | H | H | 1-oxo-4-(2-thienyl)-n-butyl |
| 8 | Me | H | H | 1-oxo-2-phenoxy-n-propyl |
| 9 | Me | H | H | 1-oxo-2-phenyl-ethyl |
| 10 | Me | H | H | 1-oxo-2-(phenylthio)ethyl |
| 11 | Me | H | 1-oxo-2-(phenylthio)ethyl | H |
| 12 | Me | H | 1-oxo-2-(phenylthio)ethyl | 1-oxo-2-(phenylthio)ethyl |
| 13 | Me | H | H | 1-oxo-2-(phenoxy)ethyl |
| 14 | Me | H | H | 2-(4-methoxyphenoxy)-1-oxo-ethyl |
| 15 | Me | H | H | 1-oxo-2-(3-thienyl)ethyl |
| 16 | Me | H | 1-oxo-2-(3-thienyl)ethyl | H |
| 17 | H | H | H | 4-(n-octyl)benzoyl |
| 18 | Me | Me | H | 4-(n-octyl)benzoyl |
| 19 | Me | Me | Me | 4-(n-octyl)benzoyl |
| 20 | Me | H | H | 4-(n-pentyl)benzoyl |
| 21 | Me | H | H | 3-(n-octyl)benzoyl |
| 22 | Me | H | H | 4-bromobenzoyl |
| 23 | Me | H | H | [4-(n-octyl)-cyclohexa-1,4-dienyl]acetyl |

TABLE I-continued

Illustrative Formula 1 Compounds[a]

| Compound No. | R | R[1] | R[2] | R[3] |
|---|---|---|---|---|
| 24 | Me | H | H | 1-naphthylacetyl |
| 26 | Me | H | H | 2-furanylacrylyl |
| 27 | Me | H | H | (2-amino-3-thiazolyl)acetyl |
| 28 | Me | H | H | (2-pyridinyl)carbonyl |
| 29 | Me | H | H | 3,4-diethoxybenzoyl |
| 30 | Me | H | H | 3-methoxy-4-(n-octyl)benzoyl |

The formula 1 compounds inhibit the growth of a broad spectrum of pathogenic bacteria, especially Gram-positive bacteria. Table II summarizes the minimal inhibitory concentrations (MIC's) at which the compounds inhibit certain ogranisms, as determined by standard agar-dilution assays.

TABLE II

In Vitro Activity of Formula 1 Compunds MIC (mcg/ml)

| Organism | 1 | 2 | 3 | 4 | 5 | 6 | 7 | 10 | 11 | 12 |
|---|---|---|---|---|---|---|---|---|---|---|
| *Staphylococcus aureus* NRRL B313 | 1 | 0.5 | 2 | 2 | 2 | 1 | 1 | 1 | 4 | 16 |
| *Staphylococcus aureus* V41 | 1 | 0.5 | 2 | 2 | 2 | 1 | 1 | 1 | 4 | 16 |
| *Staphylococcus aureus* X400 | 2 | 0.5 | 2 | 2 | 4 | 2 | 1 | 1 | 8 | 32 |
| *Staphylococcus aureus* S13E | 1 | 0.5 | 2 | 2 | 4 | 2 | 2 | 1 | 4 | 32 |
| *Staphylococcus epidermidis* EP11 | 16 | 8 | 16 | 8 | 16 | 8 | 8 | 4 | 16 | 128 |
| *Staphylococcus epidermidis* 222 | 4 | 1 | 2 | 2 | 4 | 2 | 2 | 2 | 8 | 64 |
| *Streptococcus pyrogenes* C203 | 2 | 0.25 | 1 | 1 | 2 | 1 | 1 | 0.5 | 4 | 8 |
| *Streptococcus pneumoniae* Park 1 | 2 | 0.5 | 1 | 0.5 | 2 | 1 | 0.5 | 0.5 | 2 | 8 |
| *Streptococcus faecium* ATCC 9790 | 0.5 | 0.125 | 1 | 2 | 4 | 2 | 2 | 1 | 8 | 32 |
| Streptococcus sp. group D 2041 | 1 | 0.125 | 1 | 8 | 8 | 4 | 4 | 4 | 16 | 64 |
| *Haemophilus influenzae* C.L. | —[b] | — | 128 | 128 | — | — | 128 | 128 | — | — |
| *Haemophilus influenzae* 76 | — | — | 64 | 128 | — | — | 128 | 32 | — | — |

[a]Compound numbers from Table 1
[b]— = not active at 128 mcg/ml

Some of the compounds of this invention have also shown in vivo antimicrobial activity against experimental bacterial infections. When two doses of test compound were administered to mice in experimental infections, the activity observed was measured as an $ED_{50}$ value [effective dose in mg/kg to protect 50% of the test animals: see Warren Wick, et al., *J. Bacteriol.* 81, 233–235 (1961)]. $ED_{50}$ values observed are given in Table III.

TABLE III

$ED_{50}$ Values for Formula 1 Compounds[a]

| | $ED_{50}$ (mg/kg/2) Compound Numbers[b] | | | | |
|---|---|---|---|---|---|
| Organism | 2 | 6 | 7 | 10 | vancomycin |
| *Staphylococcus aureus* | 3.78 | 3.7 | 3.05 | 2.3 | 1.8–3.7 |
| *Streptococcus pyogenes* | 1.0 | 3.2 | 3.38 | 4.45 | 0.99–1.1 |
| *Streptococcus pneumoniae* | 0.72 | 1.8 | 2.3 | 1.9 | 0.90–0.93 |

[a]Administered subcutaneously
[b]Compound numbers from Table I

Pharmaceutical formulations of formula 1 compounds and their pharmaceutically acceptable salts are also part of this invention. Thus, a formula 1 compound, preferably as a pharmaceutically acceptable salt, can be formulated for oral or parenteral administration for the therapeutic or prophylactic treatment of bacterial infections. For example, the compound can be admixed with conventional pharmaceutical carriers and excipients and used in the form of tablets, capsules, elixirs, suspensions, syrups, wafers and the like.

The compositions comprising a formula 1 compound will contain from about 0.1 to about 90% by weight of the active compound, and more generally from about 10 to about 30%.

The compositions may contain common carriers and excipients, such as corn starch or gelatin, lactose, sucrose, microcrystalline cellulose, kaolin, mannitol, dicalcium phosphate, sodium chloride and alginic acid.

Disintegrators commonly used in the formulations of this invention include croscarmellose sodium, microcrystalline cellulose, corn starch, sodium starch glycolate and alginic acid.

Tablet binders that can be included are acacia, methylcellulose, sodium carboxymethylcellulose, polyvinylpyrrolidone (Povidone), hydroxypropyl methylcellulose, sucrose, starch and ethylcellulose.

Lubricants that can be used include magnesium stearate or other metallic stearates, stearic acid, silicone fluid, talc, waxes, oils and colloidal silica.

Flavoring agents such as peppermint, oil of wintergreen, cherry flavoring or the like can also be used.

It may be desirable to add a coloring agent to make the dosage form more esthetic in appearance or to help identify the product.

For intravenous (IV) use, a water soluble form of the antibiotic can be dissolved in one of the commonly used intravenous fluids and administered by infusion. Such fluids as, for example, physiological saline, Ringer's solution or 5% dextrose solution can be used.

For intramuscular preparations, a sterile formulation of a suitable soluble form of the compound, for example the hydrochloride salt form, can be dissolved and administered in a pharmaceutical diluent such as Water-for-Injection, physiological-saline or 5% glucose solution. A suitable insoluble form of the compound may be prepared and administered as a suspension in an aqueous base or a pharmaceutically acceptable oil base, e.g. an ester of a long chain fatty acid such as ethyl oleate.

For oral use, a sterile formulation of a suitable form of the antibiotic, for example the hydrochloride salt form, formulated in a diluent such as distilled or deionized water, is particularly useful.

Alternatively, the unit dosage form of the antibiotic can be a solution of the antibiotic, or a salt thereof, in a suitable diluent in sterile, hermetically sealed ampoules. The concentration of the antibiotic in the unit dosage may vary, e.g. from about 1 percent to about 50 percent depending on the particular form of the antibiotic and its solubility and the dose desired by the physician.

In a further aspect, this invention provides a method for treating susceptible bacterial infections, especially those caused by Gram-positive microorganisms, in animals. The animal may be either susceptible to, or infected with, the microorganism. The method comprises administering to the animal an effective amount of a formula 1 compound or its pharmaceutically acceptable salt. In general, an effective amount of a formula 1 compound is a dose between about 0.5 and about 100 mg/kg. A preferred dose is from about 10 to about 60 mg/kg of active compound. A typical daily dose for an adult human is from about 250 mg to about 1.0 g.

In practicing this method, the antibiotic can be administered in a single daily dose or in multiple doses per day. The treatment regime may require administration over extended periods of time, e.g., for several days or for from two to three weeks. The amount per administered dose or the total amount administered will depend on such factors as the nature and severity of the infection, the age and general health of the patient, the tolerance of the patient to the antibiotic and the microorganism or microorganisms involved in the infection.

A convenient method of practicing the treatment method is to administer the antibiotic via IV infusion. In this procedure a sterile formulation of a suitable soluble salt of the antibiotic is incorporated in a physiological fluid, such as 5% dextrose solution, and the resulting solution is infused slowly IV. Alternatively, the piggyback method of IV infusion can also be used.

In another embodiment, this invention relates to methods of increasing feed-utilization efficiency in poultry, swine, sheep and cattle, of promoting growth rates in cattle raised for meat production and of enhancing milk production in lactating ruminants. For increasing feed-utilization efficiency and promoting growth, a formula 1 compound is administered orally in a suitable feed in an amount of from about 2 to about 200 grams per ton of total feed. For beef cattle, for example, a range of about 12 to 3000 mg/head/day is suitable. For enhancing milk production in lactating ruminants, oral administration of a daily amount of from about 0.04 to about 16 mg/kg of body weight (or about 25 to about 5000 mg/ruminant/day) is suggested.

· The following examples are provided to illustrate this invention. To simplify discussion, "$N^{van}$" is used to indicate the nitrogen on vancosamine and "$N^{leu}$" is used to indicate the nitrogen in the leucine group. Reactions were monitored by analytical high performance liquid chromatography (HPLC), using a Water's Bondapak $C_{18}$ column with a gradient solvent system of $CH_3CN/H_2O$ and 0.2% triethylamine maintained at pH 3 with phosphoric acid and detecting with UV.

EXAMPLE 1

Preparation of
$N^{van}$-[1-oxo-2-(phenylthio)ethyl]vancomycin
(Compound 10),
$N^{leu}$-[1-oxo-2-(phenylthio)ethyl]vancomycin
(Compound 11) and
$N^{van},N^{leu}$-di-[1-oxo-2-(phenylthio)ethyl]vancomycin
(Compound 12)

Vancomycin free base (5.14 g, 3.55 mmoles) was dissolved in DMF (50 mL). 2,4,5-trichlorophenylthiophenoxyacetyl ester (1.63 g, 4.71 mmoles) was added. The reaction mixture was stirred at 70° C. for two hours. The reaction mixture was evaporated under vacuum to a reduced volume. An equal volume of water was added, and the mixture was freeze-dried.

The material thus obtained was triturated with $CH_2Cl_2$ and filtered to give an insoluble residue (6.5 g). A portion of this (2 g) was purified by HPLC, using a Waters Prep Pak/500 column. The column was eluted with an acetonitrile-water system containing 1% pyridinium acetate and was monitored using a UV detector at 280 nm. This separation gave compound 10 (570 mg, 32.66% yield), compound 11 (178 mg, 10.2% yield) and compound 12 (395.8 mg, 22.67% yield). The products were confirmed by fast atom bambardment mass spectrometry.

EXAMPLES 3–12

The procedure described in Example 1, but using varying amounts of the appropriate starting active esters, was used to prepare mono-$N^{van}$-, mono-$N^{leu}$- and di-$N^{van}$, $N^{leu}$-acyl derivatives. Reaction times varied from one hour to four hours. A shorter reaction time and slight excess of active ester favored formation of the mono-$N^{van}$-acyl derivatives. A longer reaction time and a large excess of active ester favored formation of the di-$N^{van},N^{leu}$-acyl-derivatives. Thus, depending on the conditions, all three derivatives were not always favored in each reaction.

The following compounds were thus prepared:

| Compound | Name |
| --- | --- |
| 1 | $N^{van}$—[4-(n-octyloxy)benzoyl]vancomycin |
| 2 | $N^{van}$—[4-(n-octyl)benzoyl]vancomycin |
| 3 | $N^{leu}$—[4-(n-octyl)benzoyl]vancomycin |
| 4 | $N^{van}$—(4-methoxybenzoyl)vancomycin |
| 5 | $N^{leu}$—(4-methoxybenzoyl)vancomycin |
| 6 | $N^{van}$—(1-oxo-3-phenoxy-n-butyl)vancomycin |
| 7 | $N^{van}$—[1-oxo-3-(2-thienyl)-n-butyl]vancomycin |
| 8 | $N^{van}$—(1-oxo-2-phenoxy-n-propyl)vancomycin |
| 9 | $N^{van}$—(1-oxo-2-phenylethyl)vancomycin |
| 13 | $N^{van}$—[1-oxo-2-(phenoxy)ethyl]vancomycin |
| 14 | $N^{van}$—[2-(4-methoxyphenoxy)-1-oxo-ethyl]vancomycin |
| 15 | $N^{van}$—[1-oxo-2-(3-thienyl)ethyl]vancomycin |

EXAMPLES 13–27

Using the procedure described in Example 1 (with the appropriate starting active ester), the following compounds can be prepared:

$N^{van}$-[4-(tert-butyl)benzoyl]vancomycin
$N^{van}$-[4-(n-decyl)benzoyl]vancomycin
$N^{van}$-[4-(n-hexyloxy)benzoyl]vancomycin
$N^{van}$-[[3-(n-heptyl)-5-pyridyl]carbonyl]vancomycin
$V^{van}$-[[3-(n-octyloxy)-5-pyridyl]acetyl]vancomycin
$N^{van}$-[4-[3-(n-undecyl)-2-thienyl]butyryl]vancomycin $N^{van}$-[2-[4-(n-octyloxy)phenoxy]-1-oxo-ethyl]vancomycin
$N^{van}$-[4-(n-octyl)benzoyl]-A51568A
$N^{van}$-[4-(4-methylpentyl)benzoyl]-A51568A
$N^{leu}$-[4-(n-octyloxy)benzoyl]-A51568A
$N^{van}$-[4-(n-octylthio)benzoyl]-A51568B
$N^{van}$-[1-oxo-10-phenoxy-n-decyl]-A51568B
$N^{leu}$-[4-(n-heptyloxy)benzoyl]-A51568B
$N^{van}$-[4-(n-octyl)benzoyl]-M43D
$N^{van}$-[4-(n-octyloxy)benzoyl]-M43D
$N^{van}$-[[4-(n-octyl)-1-cyclohexadienyl]carbonyl]vancomycin
$N^{van}$-[[4-(n-octyloxy)-2-furyl]acetyl]vancomycin
$N^{van}$-[(7-methoxy-2-naphthyl)acetyl]vancomycin
$N^{van}$-[(2-amino-4-thiazolyl)acetyl]vancomycin Table IV summarizes certain physical characteristics of the exemplified compounds.

TABLE IV

Physical Characteristics of Formula 1 Compounds[a,b]

| Compound No. | $R^2$ | $R^3$ | HPLC Gradient System[c] | HPLC Retention Time (min.) | FDMS Parent Ion $(m^+ + 1)$ |
|---|---|---|---|---|---|
| 1 | H | 4-($C_8H_{17}O$)-C$_6$H$_4$-C(O)– | A | 14.4 | 1680 |
| 2 | H | 4-($C_8H_{17}$)-C$_6$H$_4$-C(O)– | A | 20.5 | 1664 |
| 3 | 4-($C_8H_{17}$)-C$_6$H$_4$-C(O)– | H | A | 24.97 | 1664 |
| 4 | H | 4-(MeO)-C$_6$H$_4$-C(O)– | A | 12.76 | 1582 |
| 5 | 4-(MeO)-C$_6$H$_4$-C(O)– | H | A | 14.98 | 1582 |
| 6 | H | C$_6$H$_5$-O(CH$_2$)$_3$-C(O)– | B | 18.08 | 1610 |
| 7 | H | (2-thienyl)-(CH$_2$)$_3$-C(O)– | B | 17.8 | 1600 |
| 10 | H | C$_6$H$_5$-S-CH$_2$-C(O)– | B | 16.9–17.1 | 1598 |
| 11 | C$_6$H$_5$-S-CH$_2$-C(O)– | H | B | 20.6 | 1598 |
| 12 | C$_6$H$_5$-S-CH$_2$-C(O)– | C$_6$H$_5$-S-CH$_2$-C(O)– | B | 24.7 | 1748 |

[a] Compound numbers from Table 1
[b] R = Me; $R^1$ = H is exemplified compounds
[c] Water's Bondapak C$_{18}$ Column; UV detection at 280 nm; CH$_3$CN/H$_2$O/0.2% triethylamine buffer solvent system in the following gradients:

TABLE IV-continued
Physical Characteristics of Formula 1 Compounds[a,b]

| Compound No. | R[2] | R[3] | HPLC Gradient System[c] | HPLC Retention Time (min.) | FDMS Parent Ion (m[+] + 1) |
|---|---|---|---|---|---|

| System | Gradient |
|---|---|
| A | 5% ⟶ 80% |
| B | 5% ⟶ 50% |

We claim:

1. A compound of the formula:

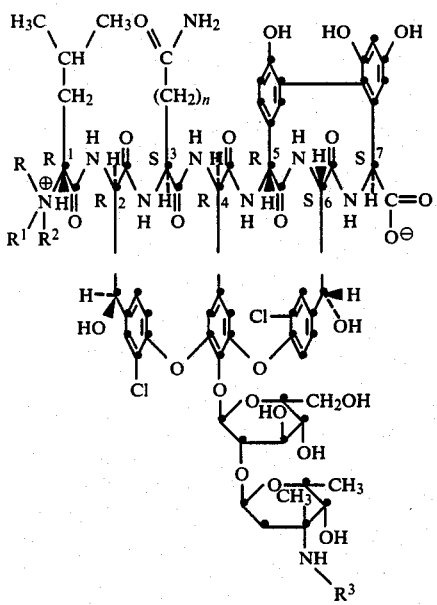

wherein

R and R[1] are hydrogen or methyl;
R[2] is methyl or R[3];
R[3] is hydrogen or an acyl group of the formula

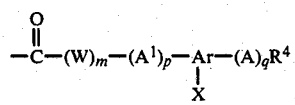

wherein

Ar is a group selected from phenyl, cyclohexadienyl, cyclohexenyl, naphthyl, thienyl, furyl, thiazolyl or pyridinyl;
A is divalent oxygen, sulfur, sulfinyl, or sulfonyl;
A[1] is A or —NH—;
X is hydrogen, chloro, bromo, iodo, nitro, $C_1$-$C_3$-alkyl, hydroxy, $C_1$-$C_3$-alkoxy, mercapto, $C_1$-$C_3$-alkylthio, carbamoyl, $C_1$-$C_3$-alkylcarbamoyl, $C_1$-$C_4$-alkoxycarbonyl, $C_1$-$C_4$-alkanoyl, carboxy, or $R_5R_6N$—;
R[4] is hydrogen, $C_1$-$C_{18}$-alkyl or $C_2$-$C_{18}$-alkenyl;
R[5] and R[6] indepedently are hydrogen or $C_1$-$C_4$-alkyl, or
R[5] is hydrogen and R[6] is an amino-protecting group;
W is $C_1$-$C_{10}$-alkylene or $C_2$-$C_{10}$-alkenylene;
n is 1 or 2; and
m, p and q are 0 or 1,
provided that: (1) the sum of the carbon atoms in the R[4] and W groups cannot exceed 21; (2) when X is mercapto, A and A[1] cannot be sulfinyl or sulfonyl; (3) when A and A[1] are sulfinyl or sulfonyl, they must be in equal oxidation states; (4) at least one of R[2] and R[3] must be other than hydrogen; (5) if m=0, p must=0; and (6) when n is 2, R and R[1] must be hydrogen; and its salts.

2. A compound of claim 1 wherein R is methyl and R[1] and R[2] are hydrogen.

3. A compound of claim 1 wherein R and R[1] are methyl and R[2] is hydrogen.

4. A compound of claim 1 wherein R, R[1] and R[2] are methyl.

5. A compound of claim 1 wherein R, R[1] and R[2] are hydrogen.

6. A compound of claim 5 wherein n is 1.

7. A compound of claim 5 wherein n is 2.

8. A compound of claim 1 wherein R[2] is hydrogen and R[3] is a specified acyl group.

9. A compound of claim 1 wherein R[3] is hydrogen and R[2] is a specified acyl group.

10. A compound of claim 1 wherein Ar is phenyl.

11. A compound of claim 10 wherein R[4] is $C_1$-$C_{18}$-alkyl.

12. A compound of claim 10 wherein A is oxygen.

13. A compound of claim 8 wherein m and p=0.

14. The compound of claim 8 which is N[van]-[4-(n-octyloxy)benzoyl]vancomycin.

15. The compound of claim 8 which is N[van]-[4-(n-octyl)benzoyl]vancomycin.

16. A compound of claim 1 wherein the salts are pharmaceutically acceptable.

17. A compound of claim 2 wherein the salts are pharmaceutically acceptable.

18. A compound of claim 8 wherein the salts are pharmaceutically acceptable.

19. A composition useful for the control of susceptible bacterial infections comprising an effective amount of a compound of claim 16 and a suitable pharmaceutical vehicle.

20. A composition useful for the control of susceptible bacterial infections comprising an effective amount of a compound of claim 17 and a suitable pharmaceutical vehicle.

21. A composition useful for the control of susceptible bacterial infections comprising an effective amount of a compound of claim 18 and a suitable pharmaceutical vehicle.

22. A method for treating susceptible bacterial infections which comprises administering an effective amount of a composition of claim 19 to an animal.

23. A method for treating susceptible bacterial infections which comprises administering an effective amount of a composition of claim 20 to an animal.

24. A method for treating susceptible bacterial infections which comprises administering an effective amount of a composition of claim 21 to an animal.

* * * * *

UNITED STATES PATENT AND TRADEMARK OFFICE
CERTIFICATE OF CORRECTION

PATENT NO. : 4,643,987

DATED : February 17, 1987

INVENTOR(S) : Ramakrishnan Nagarajan, et al

It is certified that error appears in the above-identified patent and that said Letters Patent is hereby corrected as shown below:

Columns 1 and 2, lines 12 through 33; columns 3 and 4, lines 27 through 40; and column 13, lines 19 through 30:

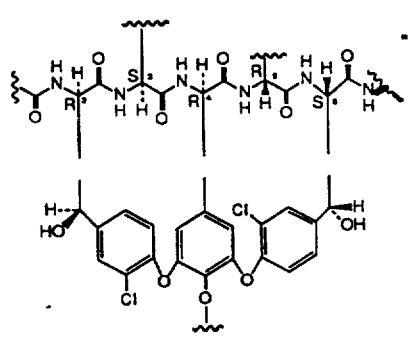 should read 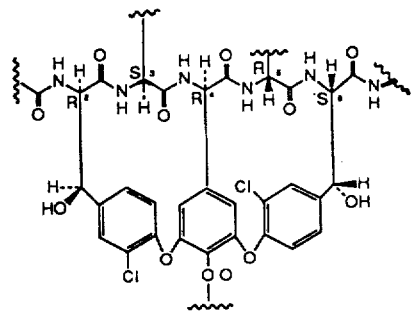

Column 13, line 61: "indepedently" should read --independently--.

Signed and Sealed this

Eighteenth Day of December, 1990

Attest:

HARRY F. MANBECK, JR.

Attesting Officer

Commissioner of Patents and Trademarks